US005739352A

United States Patent [19]
Barner et al.

[11] Patent Number: 5,739,352
[45] Date of Patent: Apr. 14, 1998

[54] PROCESS FOR PREPARING CARBOXYLIC ACIDS

[75] Inventors: Bruce Armin Barner, Alum Creek; Jonathan Joshua Kurland, Charleston, both of W. Va.

[73] Assignee: United Carbide Chemicals & Plastics Technology Corporation, Danbury, Conn.

[21] Appl. No.: 545,308

[22] Filed: Oct. 19, 1995

[51] Int. Cl.[6] .................... C07D 209/12; C07C 51/255
[52] U.S. Cl. .................... 548/472; 549/71; 562/418; 562/460; 562/466; 562/496
[58] Field of Search .................... 548/472; 549/71; 562/418, 460, 466, 496

[56] References Cited

U.S. PATENT DOCUMENTS

| | | | |
|---|---|---|---|
| 3,927,122 | 12/1975 | Bourdin et al. | 260/621 |
| 4,138,417 | 2/1979 | Ukihashi et al. | 260/406 |
| 4,249,019 | 2/1981 | Tamura et al. | 560/208 |
| 5,237,092 | 8/1993 | Tanaka et al. | 560/238 |
| 5,278,321 | 1/1994 | Tanaka et al. | 549/272 |

FOREIGN PATENT DOCUMENTS

| | | |
|---|---|---|
| 2040742 | 10/1991 | Canada . |
| 0 453 356 | 10/1991 | European Pat. Off. . |
| 073106 | 6/1977 | Japan . |
| 1521906 | 8/1978 | United Kingdom . |

OTHER PUBLICATIONS

Matsuoka et al., Chemical Abstracts, vol. 115:256431p., 1991.

Dinizo et al., J. Am. Chem. Soc., vol. 99:1, pp. 182–186, 1977.

Dodd, R.H.; Le Hyaric, M. "The Oxidation of Aromatic Aldehydes to Carboxylic Acids Using Hydrogen Peroxide in Formic Acid" *Synthesis* 1993, 295.

Dodd, R.H.; Doisy, X.; Potier, P. "Synthesis and Pharmacological of a Pyrido[3',4':5,4]Pyrrolo[1,2-c]-[1,4]Benzodiazepine-3, 10-Dione, a New Benzodiazepine-..." *Heterocycles* 1989, 28 (2), 1101.

Choi, J.-K.; Chang, Y.-K.; Hong, S.Y. "Catalytic Oxidation of Aldehydes to Carboxylic Acids With Hydrogen Peroxide as Oxidant" *Tetrahedron Lett.* 1988, 29 (16), 1967.

Hiatt, R.R.; Glover, L.C.; Mosher, H.M. "Concerted Mechanism and Phase Effects in Decompositions of Alkyl Peroxy Esters" *J. Am. Chem. Soc.* 1975, 97 (6), 1556.

T. Maki. "Alpha–branched Aliphatic Carboxylic Acids" *Chem. Abstr.* 90:168072g, 1979.

Larkin, D.R. "The Role of Catalysts in the Air Oxidation of Aliphatic Aldehydes" *J. Org. Chem.* 1990, 55, 1565–1568.

*Primary Examiner*—Joseph McKane
*Attorney, Agent, or Firm*—Gerald L. Coon

[57] ABSTRACT

This invention relates to a process for preparing carboxylic acids by oxidizing an aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the carboxylic acid. Such carboxylic acids have utility for example as chemical intermediates.

5 Claims, No Drawings

PROCESS FOR PREPARING CARBOXYLIC ACIDS

BRIEF SUMMARY OF THE INVENTION

RELATED APPLICATIONS

The following are related, commonly assigned applications filed on an even date herewith: U.S. patent application Ser. No. 545,349 and U.S. patent application Ser. No. 547,702, both of which are incorporated herein by reference.

TECHNICAL FIELD

This invention relates to a process for preparing carboxylic acids by oxidizing an aldehyde with a peracid in the presence of an amine and/or amine N-oxide catalyst to produce the carboxylic acid.

BACKGROUND OF THE INVENTION

Various processes for oxidizing an aldehyde with a peracid to produce a carboxylic acid have been described in the art. However, there is a continuing need to provide improved processes for preparing carboxylic acids by oxidizing an aldehyde with a peracid to produce the carboxylic acids in which the amount of formate byproducts is reduced or eliminated and the oxidation efficiency is enhanced.

DISCLOSURE OF THE INVENTION

This invention relates to a process for producing a carboxylic acid which process comprises oxidizing an aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the carboxylic acid, wherein said amine and/or amine N-oxide catalyst has a basicity sufficient to catalyze said oxidizing of the aldehyde to the carboxylic acid, and provided that when the peracid is performic acid, the aldehyde is other than an aromatic or heteroaromatic aldehyde.

This invention also relates to a process for producing a carboxylic acid which process comprises: (1) reacting an olefinically unsaturated compound with carbon monoxide and hydrogen in the presence of a metal-ligand complex catalyst to produce an aldehyde; and (2) oxidizing the aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the carboxylic acid, wherein said amine and/or amine N-oxide catalyst has a basicity sufficient to catalyze said oxidizing of the aldehyde to the carboxylic acid, and provided that when the peracid is performic acid, the aldehyde is other than an aromatic or heteroaromatic aldehyde.

This invention further relates to a process for producing a carboxylic acid which process comprises: (1) reacting an olefinically unsaturated organic compound with carbon monoxide and hydrogen in the presence of a rhodium-ligand complex catalyst to produce an aldehyde; and (2) oxidizing the aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the carboxylic acid, wherein said amine and/or amine N-oxide catalyst has a basicity sufficient to catalyze said oxidizing of the aldehyde to the carboxylic acid, and provided that when the peracid is performic acid, the aldehyde is other than an aromatic or heteroaromatic aldehyde.

DETAILED DESCRIPTION

Aldehyde-Forming Reaction

The aldehyde employed in the process of this invention can be prepared by conventional methods known in the art. The preferred aldehyde-forming reaction is a hydroformylation reaction. The hydroformylation reaction involves the production of aldehydes by reacting an olefinic compound with carbon monoxide and hydrogen in the presence of a solubilized metal-organophosphorus complex catalyst and free organophosphorus ligand in a liquid medium that also contains a solvent for the catalyst and ligand. The process may be carried out in a continuous single pass mode in a continuous gas recycle manner or more preferably in a continuous liquid catalyst recycle manner as described below. The hydroformylation processing techniques employable herein may correspond to any known processing techniques employed in conventional hydroformylation reactions.

The hydroformylation reaction mixture starting materials employable herein includes any organic solution derived from any corresponding hydroformylation process that contains at least some amount of four different main ingredients or components, i.e., the aldehyde product, a metal-organophosphorus ligand complex catalyst, free organophosphorus ligand and an organic solubilizing agent for said catalyst and said free ligand, said ingredients corresponding to those employed and/or produced by the hydroformylation process from whence the hydroformylation reaction mixture starting material may be derived. By "free ligand" is meant organophosphorus ligand that is not complexed with (tied to or bound to) the metal, e.g., rhodium atom, of the complex catalyst. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation by-products, as well as other inert co-solvent type materials or hydrocarbon additives, if employed.

In an embodiment of this invention, certain additives can be employed in the hydroformylation reaction mixture to stabilize the organophosphorus ligands against degradation. For example, epoxides can be added to the hydroformylation reaction mixture to reduce degradation of the organophosphite ligand as described in U.S. Pat. No. 5,364,950, the disclosure of which is incorporated herein by reference.

The catalyst useful in the hydroformylation reaction includes a metal-ligand complex catalyst. The permissible metals which make up the metal-ligand complexes include Group VIII metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group IB metals selected from copper (Cu), silver (Ag), gold (Au) and mixtures thereof, and also Group VIB metals selected from chromium (Cr), molybdenum (Mo), tungsten (W) and mixtures thereof, and also Group VA metals selected from arsenic (As) and antimony (Sb) and mixtures thereof. Mixtures of metals from Group VIII, Group IB, Group VIB and Group VA may be used in this invention. The permissible organophosphorus ligands which make up the metal-ligand complexes include organophosphines, e.g., triorganophosphines, and organophosphites, e.g., mono-, di-, tri- and polyorganophosphites. Other permissible organophosphorus ligands include, for example, organophosphonites, organophosphinites, organophosphorus amides and the like. Mixtures of such ligands may be employed if desired in the metal-ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, i.e., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst and have an undue adverse effect on catalyst performance. It is preferred in the metal-ligand complex catalyzed hydroformylation reactions that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per one molecule of metal, e.g., rhodium. As noted above, it is considered that the catalytic species of the preferred catalyst employed in the hydroformylation reaction may be complexed with carbon monoxide and hydrogen in addition to the organophosphorus ligands in view of the carbon monoxide and hydrogen gas employed by the hydroformylation reaction.

Among the organophosphines that may serve as the ligand of the metal-organophosphine complex catalyst and/or free organophosphine ligand of the hydroformylation reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl biphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substitutent that does not unduly adversely affect the desired result of the hydroformylation reaction. The organophosphine ligands employable in the hydroformylation reaction and/or methods for their preparation are known in the art.

Illustrative triorganophosphine ligands may be represented by the formula:

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater, the most preferred hydrocarbon radical being phenyl, ($C_6H_5$—). Illustrative substituent groups that may be present on the aryl radicals include, e.g., alkyl radicals, alkoxy radicals, silyl radicals such as —Si($R^2$)$_3$; amino radicals such as —N($R^2$)$_2$; acyl radicals such as —C(O)$R^2$; carboxy radicals such as —C(O)O$R^2$; acyloxy radicals such as —OC(O)$R^2$; amido radicals such as —C(O)N($R^2$)$_2$ and —N($R^2$)C(O)$R^2$; ionic radicals such as —SO$_3$M wherein M represents inorganic or organic cationic atoms or radicals; sulfonyl radicals such as —SO$_2R^2$; ether radicals such as —O$R^2$; sulfinyl radicals such as —SO$R^2$; sulfenyl radicals such as —S$R^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —N($R^2$)$_2$, each $R^2$ taken together can also represent a divalent bridging group that forms a heterocyclic radical with the nitrogen atom and in amido substituents such as C(O)N($R^2$)$_2$ and —N($R^2$)C(O)$R^2$ each —$R^2$ bonded to N can also be hydrogen. Illustrative alkyl radicals include, e.g., methyl, ethyl, propyl, butyl and the like. Illustrative aryl radicals include, e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, e.g., triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphenylphosphine, tribenzylphosphine as well as the alkali and alkaline earth metal salts of sulfonated triphenylphosphines, e.g., of (tri-m-sulfophenyl)phosphine and of (m-sulfophenyl)diphenyl-phosphine and the like. The most preferred organophosphine ligands are triphenylphosphine (TPP) and the sodium salt of 3-(diphenylphosphino) benzene sulfonic acid (TPPMS-Na), while the most preferred catalysts are a rhodium-TPP complex and a rhodium-TPPMS-Na complex.

More particularly, illustrative metal-organophosphine complex catalyts and illustrative free organophosphine ligands include, e.g., those disclosed in U.S. Pat. Nos. 3,527,809; 4,148,830; 4,247,486; 4,283,562; 4,400,548; 4,482,749 and 4,861,918, the disclosures of which are incorporated herein by reference.

Among the organophosphites that may serve as the ligand of the metal-organophosphite complex catalyst and/or free organophosphite ligand of the hydroformylation reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

(II)

wherein $R^3$ represents a substituted or unsubstituted trivalent hydrocarbon radical containing from 6 to 18 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, e.g., in U.S. Pat. No. 4,567,306, the disclosure of which is incorporated herein by reference.

Representative diorganophosphites may include those having the formula:

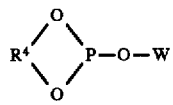
(III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, e.g., alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, e.g., in U.S. Pat. Nos. 3,415,906 and 4,567,302 and the like, the disclosures of which are incorporated herein by reference. Illustrative divalent aromatic radicals include, e.g., arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, e.g., in U.S. Pat. Nos. 4,599,206 and 4,717,775, and the like, the disclosures of which are incorporated herein by reference.

Representative of a more preferred class of diorganophosphites are those of the formula:

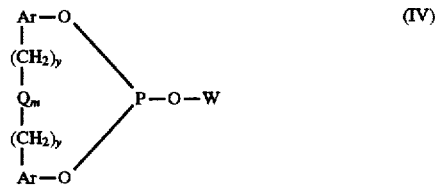
(IV)

wherein W is as defined above, each Ar is the same or different and represents a substituted or unsubstituted aryl radical, each y is the same or different and is a value of 0 or 1, Q represents a divalent bridging group selected from $—C(R^5)_2—$, $—O—$, $—S—$, $—NR^6—$, $Si(R^7)_2—$ and $—CO—$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, e.g., in U.S. Pat. Nos. 4,599,206 and 4,717,775, the disclosures of which are incorporated herein by reference.

Representative triorganophosphites may include those having the formula:

(V)

wherein each $R^8$ is the same or different and is a substituted or unsubstituted monovalent hydrocarbon radical, e.g., an alkyl or aryl radical. Suitable hydrocarbon radicals may contain from 1 to 24 carbon atoms or greater and may include those described above for $R^1$ in formula (I).

Representative organopolyphosphites contain two or more tertiary (trivalent) phosphorus atoms and may include those having the formula:

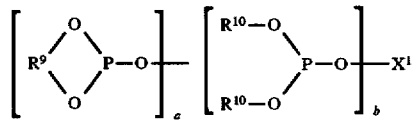
(VI)

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-Qm-alkylene, cycloalkylene, arylene, bisarylene, arylene-alkylene, and arylene-$(CH_2)_y$-Qm-$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, e.g., in U.S. Pat. Nos. 3,415,906; 4,567,306; 4,599,206; 4,769,498; 4,717,775; 4,885,401; 5,202,297; 5,264,616 and 5,364,950, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

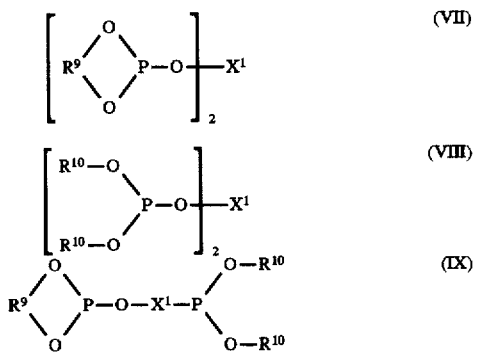

wherein each $R^9$, R10 and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Phosphite ligands of such formulas (VI) to (IX) may be found disclosed, e.g., in said U.S. Pat. Nos. 4,668,651; 4,748,261; 4,769,498; 4,885,401; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

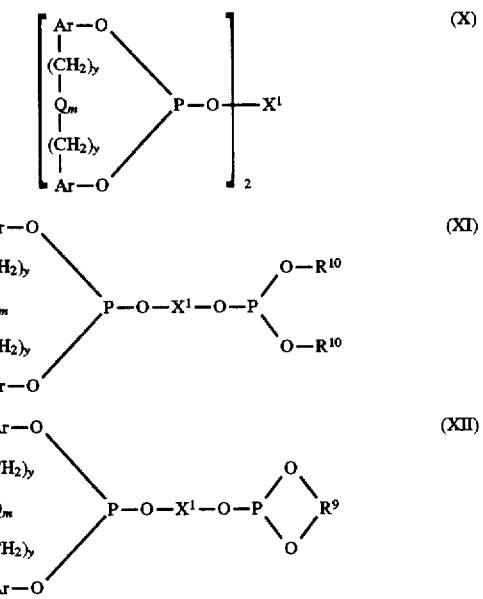

wherein Ar, Q, $R^9$, $R^{10}$, $X^1$, m and y are as defined above. Most preferably $X^1$ represents a divalent aryl-$(CH_2)_y$-$(Q)_m$-$(CH_2)_y$-aryl radical wherein each y individually has a value of 0 or 1; m has a value of 0 or 1 and Q is —$C(R^5)_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above formulas (VI) to (XII) may be an ionic phosphite, i.e., may contain one or more ionic moieties selected from the group consisting of:

$SO_3M$ wherein M represents inorganic or organic cationic atoms or radicals, $PO_3M$ wherein M represents inorganic or organic cationic atoms or radicals, $N(R^{11})_3X^2$ wherein each $R^{11}$ is the same or different and represents a hydrocarbon radical containing from 1 to 30 carbon atoms, e.g. alkyl, aryl, alkaryl, aralkyl, and cycloalkyl radicals, and $X^2$ represents inorganic or organic anionic atoms or radicals, $CO_2M$ wherein M represents inorganic or organic cationic atoms or radicals, as described, e.g., in U.S. Pat. Nos. 5,059,710; 5,113,022 and 5,114,473, the disclosures of which are incorporated herein by reference. Thus, if desired, such phosphite ligands may contain from 1 to 3 such ionic moieties, while it is preferred that only one such ionic moiety be substituted on any given aryl moiety in the phosphite ligand when the ligand contains more than one such ionic moiety. As suitable counter-ions, M and $X^2$, for the anionic moieties of the ionic phosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation and quaternary ammonium cations. Suitable anionic atoms of radicals include, for example, sulfate, carbonate, phosphate, chloride, acetate, oxalate and the like.

Of course any of the $R^9$, $R^{10}$, $X^2$ and Ar radicals of such non-ionic and ionic organophosphites of formulas (VI) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —Si$(R^{12})_3$; amino radicals such as —N$(R^{12})_2$; phosphine radicals such as -aryl-P$(R^{12})_2$; acyl radicals such as —C(O)$R^{12}$; acyloxy radicals such as —OC(O)$R^{12}$; amido radicals such as —CON$(R^{12})_2$ and —N$(R^{12})$COR$^{12}$; sulfonyl radicals such as —SO$_2$R$^{12}$; alkoxy radicals such as —OR$^{12}$; sulfinyl radicals such as —SOR$^{12}$; sulfenyl radicals such as —SR$^{12}$; phosphonyl radicals such as —P(O)$(R^{12})_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N$(R^{12})_2$ each $R^{12}$ taken together can also represent a divalent bridging group that forms a heterocyclic radical with the nitrogen atom, and in amido substituents such as —C(O)N$(R^{12})_2$ and —N$(R^{12})$COR$^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —(OCH$_2$CH$_2$)$_2$OCH$_3$, —(OCH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$),and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, -P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of organobisphosphite ligands include, e.g., the following:

2-t-butyl-4-methoxyphenyl(3,3'- di-t-butyl-5,5'- dimethoxy-1,1'-biphenyl-2,2'-diyl)phosphite having the formula:

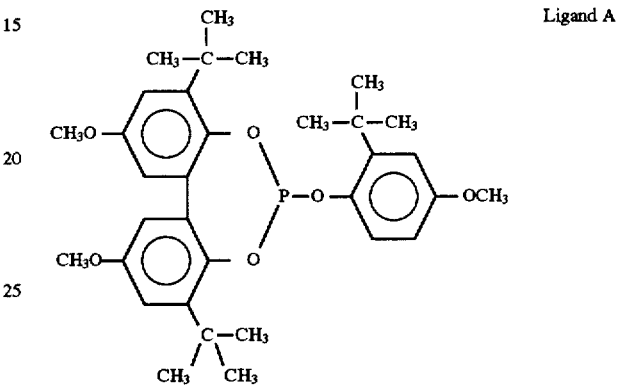

Ligand A 6,6'-[[3,3, '-bis(1,1-dimethylethyl)-5,5'-dimethoxy-[1,1'-biphenyl]-2,2'-diyl]bis(oxy)]bis-dibenzo[d,f][1,3,2] dioxaphosphepin having the formula:

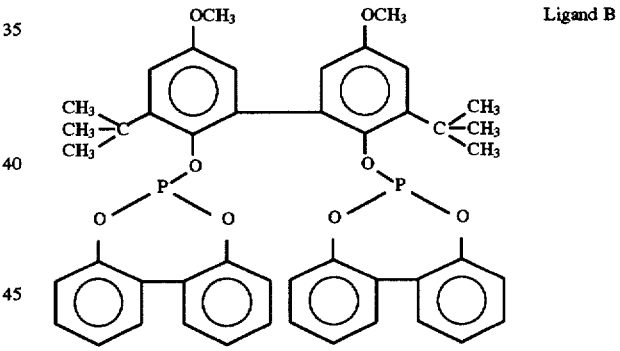

Ligand B 6,6'-[[3,3', 5,5'-tetrakis(1,1-dimethylpropyl)-[1,1'-biphenyl] -2,2'-diyl]bis(oxy)]bis-dibenzo[d,f][1,3,2]dioxaphosphepin having the formula:

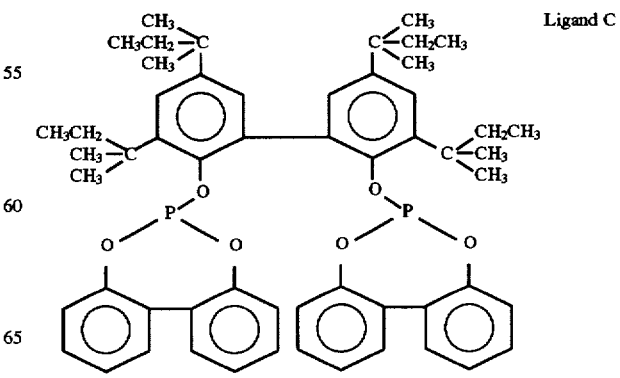

Ligand C 6,6'- [[3,3', 5,5'-tetrakis(1,1-dimethylethyl)-[1,1'-biphenyl]-2,2'-diyl]bis(oxy)]bis-dibenzo[d,f][1,3,2]dioxaphosphepin having the formula:

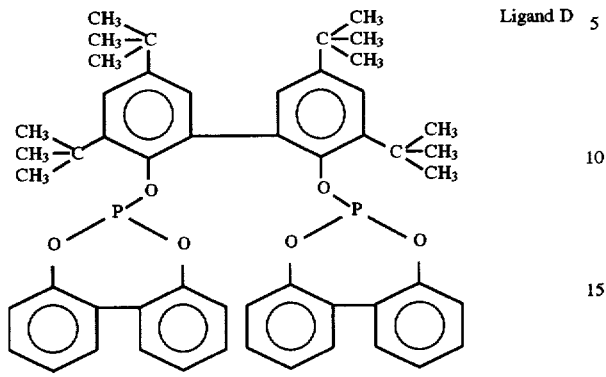

Ligand D

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2] dioxaphosphepin having the formula:

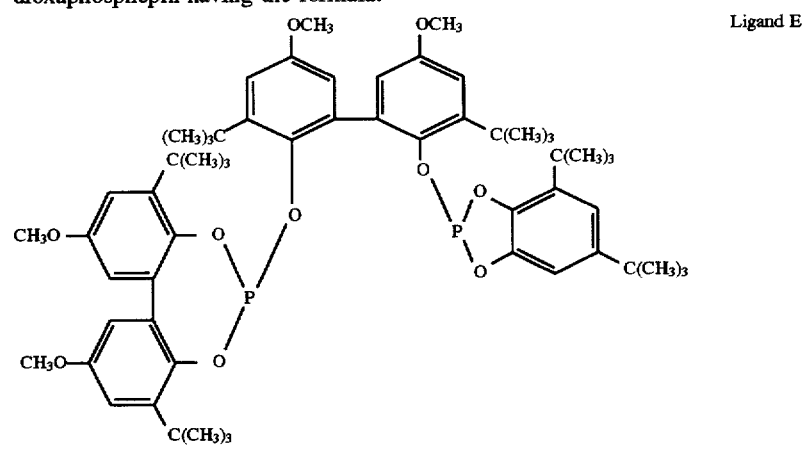

Ligand E

6-[[2'-[1,3,2-benzodioxaphosphol-2yl)oxy]-3,3'-bis(1,1-dimethylethyl)-5,5'-d imethoxy[1,1'-biphenyl]-2-yl]oxy]-4,8-bis(1,1-dimethylethyl)-2,10-dimethoxy-dibenzo[d,f][1,3,2]dioxaphosphepin having the formula:

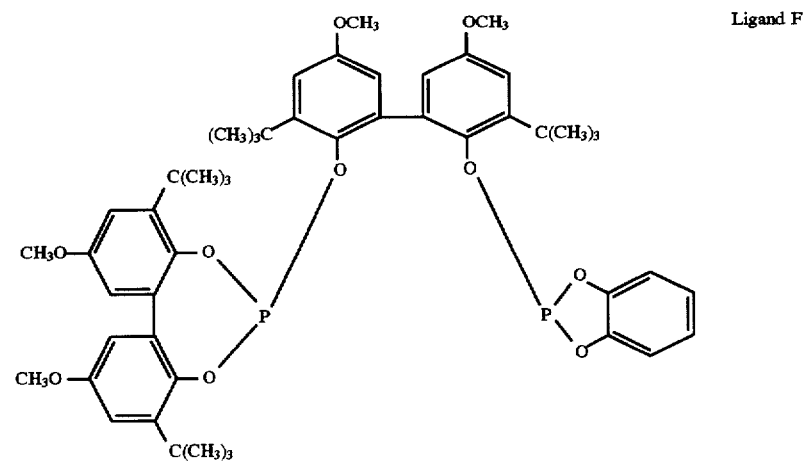

Ligand F

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand G

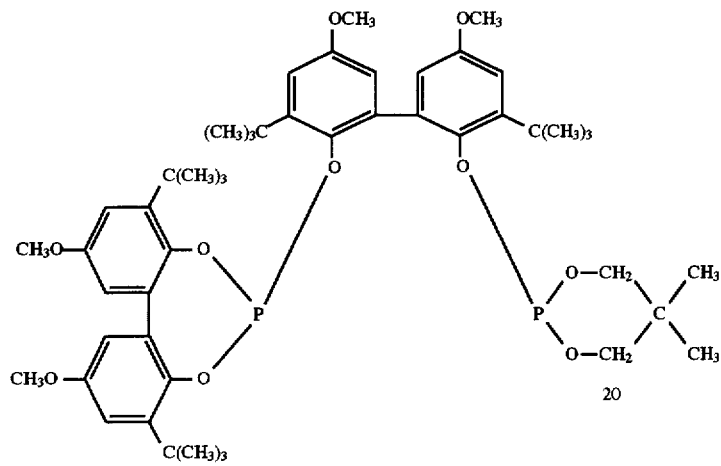

2'-[[4,8-bis (1,1-dimethylethyl)-2,10-dimethoxydibenzo-[d,f][1,3,2]dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

Ligand H

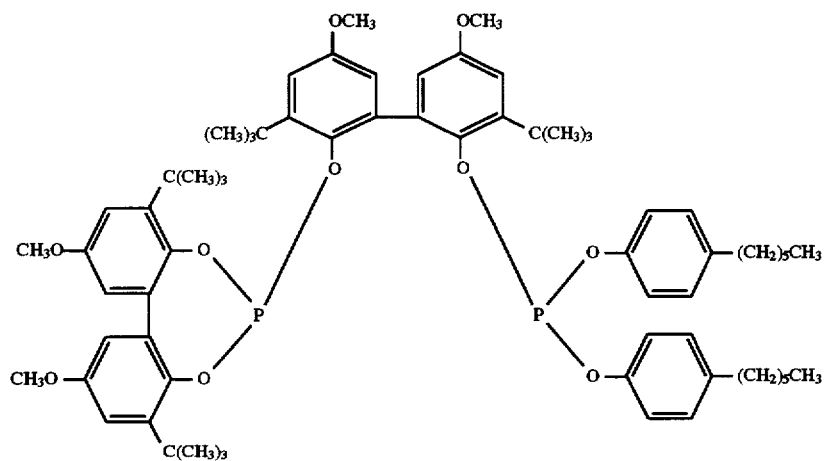

2-[[2-[[4,8,-bis(1,1-dimethylethyl), 2,10-dimethoxydibenzo [d,f][1,3,2]dioxophosphepin-6-yl]oxy]-3-(1,1-dimethylethyl)-5-methoxyphenyl]methyl]-4-methoxy,6-(1,1-dimethylethyl)phenyl diphenyl ester of phosphorous acid having the formula:

Ligand I

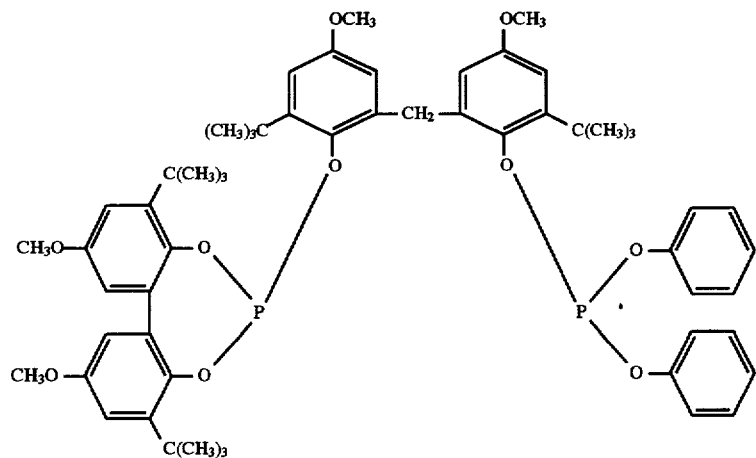

3-methoxy-1,3-cyclohexamethylene tetrakis[3,6-bis(1,1-dimethylethyl)-2-naphthalenyl]ester of phosphorus acid having the formula:

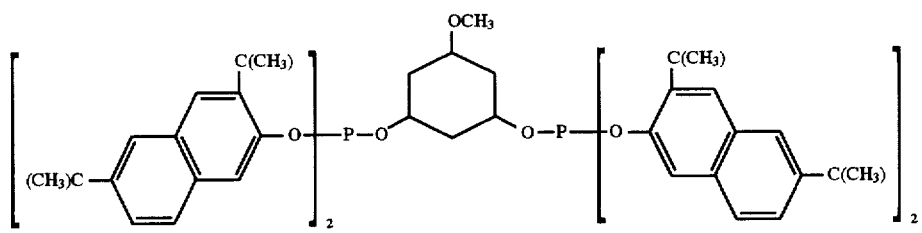

Ligand J 2,5-bis(1,1-dimethylethyl)-1,4-phenylene tetrakis[2,4-bis(1,1-dimethylethyl)phenyl]ester of phosphorous acid having the formula:

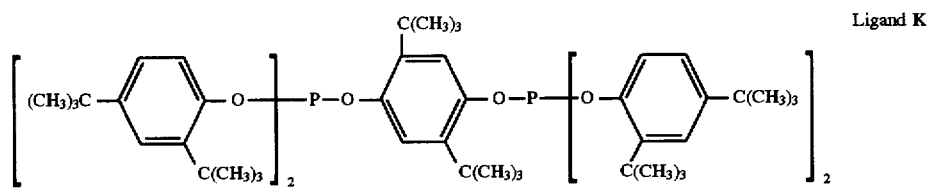

Ligand K methylenedi-2,1-phenylene tetrakis[2,4-bis(1,1-dimethylethyl)phenyl]ester of phosphorous acid having the formula:

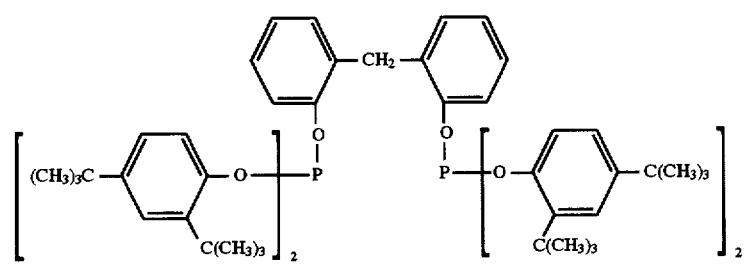

Ligand L

[1,1'-biphenyl]-2,2'-diyl tetrakis[2-(1,1-dimethylethyl)-4-methoxyphenyl]-ester of phosphorous acid having the formula:

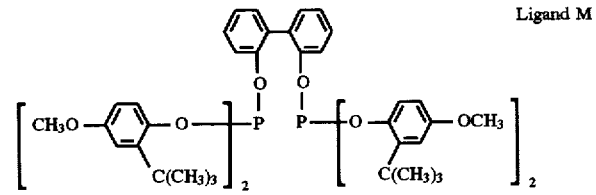

Ligand M

The metal-organophosphorus ligand complex catalysts employable in this invention may be formed by methods known in the art. For instance, preformed metal hydridocarbonyl-organophosphorus ligand catalysts may be prepared and introduced into the reaction mixture of a hydroformylation process. More preferably, the metal-organophosphorus ligand complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reactor along with excess free organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydroformylation reaction.

More particularly, a catalyst precursor composition can be formed consisting essentially of a solubilized metal-organophosphorus ligand complex precursor catalyst, an organic solvent and free organophosphorus ligand. Such precursor compositions may be prepared by forming a solution of a metal starting material, such as a metal oxide, hydride, carbonyl or salt, e.g. a nitrate, which may or may not be in complex combination with a organophosphorus ligand as defined herein. Any suitable metal starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial metal, may be complexed to the metal either prior to or in situ during the carbonylation process.

By way of illustration, the preferred catalyst precursor composition of this invention consists essentially of a solubilized rhodium carbonyl organophosphorus ligand complex precursor catalyst, an organic solvent and free organophosphorus ligand prepared by forming a solution of rhodium dicarbonyl acetylacetonate, an organic solvent and a organophosphorus ligand as defined herein. The organophosphorus ligand readily replaces one of the dicarbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorus ligand, to form the active complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor metal and hydroformylation start-up.

Accordingly, the metal-organophosphorus ligand complex catalysts used in the process of this invention consists essentially of the metal complexed with carbon monoxide and a organophosphorus ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphorus ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphorus ligand complex catalyst may be present as a result of being ligands bound to a precursor catalyst and/or as a result of in situ formation, e.g., due to the hydrogen and carbon monoxide gases employed in hydroformylation process of this invention.

As noted the hydroformylation reactions involve the use of a metal-organophosphorus ligand complex catalyst as described herein. Of course mixtures of such catalysts can also be employed if desired. The amount of metal-organophosphorus ligand complex catalyst present in the reaction medium of a given hydroformylation reaction need only be that minimum amount necessary to provide the given metal concentration desired to be employed and which will furnish the basis for at least the catalytic amount of metal necessary to catalyze the particular hydroformylation reaction involved such as disclosed e.g. in the above-mentioned patents. In general, the catalyst concentration can range from several parts per million to several percent by weight. Organophosphorus ligands can be employed in the above-mentioned catalysts in a molar ratio of generally from about 1:1 or less to about 1000:1 or greater.

In general, the organophosphorus ligand concentration in hydroformylation reaction mixtures may range from between about 0.005 and 15 weight percent based on the total weight of the reaction mixture. Preferably the ligand concentration is between 0.001 and 10 weight percent, and more preferably is between about 0.05 and 5 weight percent on that basis.

In general, the concentration of the metal in the hydroformylation reaction mixtures may be as high as about 2000 parts per million by weight based on the weight of the reaction mixture. Preferably the metal concentration is between about 50 and 1000 parts per million by weight based on the weight of the reaction mixture, and more preferably is between about 70 and 800 parts per million by weight based on the weight of the reaction mixture.

In addition to the metal-organophosphorus ligand complex catalyst, free organophosphorus ligand (i.e., ligand that is not complexed with the rhodium metal) is also present in the hydroformylation reaction medium. The free organophosphorus ligand may correspond to any of the above-defined phosphorus-containing ligands discussed above as employable herein. It is preferred that the free organophosphorus ligand be the same as the phosphorus-containing ligand of the metal-organophosphorus complex catalyst employed. However, such ligands need not be the same in any given process. The hydroformylation reaction may involve up to 100 moles, or higher, of free organophosphorus ligand per mole of metal in the hydroformylation reaction medium. Preferably the hydroformylation reaction is carried out in the presence of from about 1 to about 50 moles of phosphorus-containing ligand, and more preferably from about 1 to about 4 moles of phosphorus-containing ligand, per mole of metal present in the reaction medium; said amounts of phosphorus-containing ligand being the sum of both the amount of phosphorus-containing ligand that is bound (complexed) to the rhodium metal present and the amount of free (non-complexed) phosphorus-containing ligand present. Of course, if desired, make-up or additional phosphorus-containing ligand can be supplied to the reaction medium of the hydroformylation reaction at any time and in any suitable manner, e.g. to maintain a predetermined level of free ligand in the reaction medium.

The olefin starting material reactants that may be employed in the hydroformylation reactions include olefin compounds containing from 2 to 30, preferably 3 to 20, carbon atoms. Such olefin compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, e.g., in U.S. Pat. Nos. 4,518,809 and 4,528,403). Moreover, such olefin compounds may further contain one or more ethylenic unsaturated groups, and of course, mixtures of two or more different olefinic compounds may be employed as the starting hydroformylation material if desired. Further such olefin compounds and the corresponding aldehyde products derived therefrom may also contain one or more groups or substituents which do not unduly adversely affect the hydroformylation process or the process of this invention such as described, e.g., in U.S. Pat. Nos. 3,527,809; 4,668,651 and the like.

Illustrative olefinic unsaturated compounds are alpha-olefins, internal olefins, 1,3-dienes, alkyl alkenoates, alkenyl alkanoates, alkenyl alkyl ethers, alkenols, alkenals, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, butadiene, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, methyl pentenoate, n-propyl-7-octenoate, pentenals, e.g., 2-pentenal, 3-pentenal and 4-pentenal; pentenols, e.g., 2-pentenol, 3-pentenol and 4-pentenol; 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta-pinene, dicyclopentadiene, cyclooctadiene, camphene, linalool, and the like. Other illustrative olefinic compounds useful in the hydroformylation reaction include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described in U.S. Pat. No. 4,329,507, the disclosure of which is incorporated herein by reference.

Illustrative olefins useful in the hydroformylation reactions that can be employed to produce aldehyde mixtures include those represented by the formula:

(XIII)

wherein $R_1$, $R_2$, $R_3$ and $R_4$ are the same or different and are selected from hydrogen or a substituted or unsubstituted hydrocarbon radical, e.g., alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the olefins of this definition also include molecules of the above general formula where the R-groups are connected to form ring compounds, e.g., 3-methyl-1-cyclohexene, and the like.

Mixtures of different olefinic starting materials can be employed, if desired, in the hydroformylation reactions. More preferably the hydroformylation reactions are especially useful for the production of aldehydes, by hydroformylating alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial alpha olefins containing four or more carbon atoms may contain minor amounts of corresponding internal olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II.

The hydroformylation reaction conditions may include any suitable type hydroformylation conditions heretofore employed for producing aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 1500 psia and more preferably less than about 500 psia. The minimum total pressure being limited predominately by the amount of reactants necessary to obtain a desired rate of reaction. More specifically the carbon monoxide partial pressure of the hydroformylation process of this invention is preferable from about 1 to about 360 psia, and more preferably from about 3 to about 270 psia, while the hydrogen partial pressure is preferably about 15 to about 480 psia and more preferably from about 30 to about 300 psia. In general, the molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about −25° C. to about 200° C. In general hydroformylation reaction temperature of about 50° C. to about 120° C. are preferred for all types of olefinic starting materials. Of course, it is to be also understood that the hydroformylation reaction conditions employed will be governed by the type of aldehyde product desired.

The hydroformylation reaction is also conducted in the presence of an organic solvent for the metal-organophosphorus complex catalyst and free organophosphorus ligand. Depending on the particular catalyst and reactants employed, suitable organic solvents include, for example, alcohols, alkanes, alkenes, alkynes, ethers, aldehydes, higher boiling aldehyde condensation by-products, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene) and ethers (e.g. tetrahydrofuran (THF) and glyme). Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

Illustrative aldehyde products include e.g., propionaldehyde, n-butyraldehyde, isobutyraldehyde, n-valeraldehyde, 2-methylbutyraldehyde, hexanal, 2-methylvaleraldehyde, heptanal, 2-methylhexanal, octanal, 2-methylheptanal, nonanal, 2-methyloctanal, 2-ethylheptanal, 2-propylheptanal, 3-propylhexanal, decanal, adipaldehyde, 2-methylglutaraldehyde, 2-methyladipaldehyde, 3-methyladipaldehyde, 3-hydroxypropionaldehyde, 3-pentenal, alkyl 5-formylvalerate, 2-methylnonanal, undecanal, 2-methyldecanal, dodecanal, 2-methylundecanal, tridecanal, 2-methyltridecanal, 2-ethyldodecanal, 3-propylundecanal, pentadecanal, 2-methyltetradecanal, hexadecanal, 2-methylpentadecanal, heptadecanal, 2-methylhexadecanal, octadecanal, 2-methylheptadecanal, nonodecanal, 2-methyloctadecanal, 2-ethylheptadecanal, 3-propylhexadecanal, eicosanal, 2-methylnonadecanal, heneicosanal, 2-methyleicosanal, tricosanal, 2-methyldocosanal, tetracosanal, 2-methyltricosanal, pentacosanal, 2-methyltetracosanal, 2-ethyltricosanal, 3-propyldocosanal, heptacosanal, 2-methyloctacosanal, nonacosanal, hentriacontanal, 2-methyltriacontanal, and the like.

As indicated above, the hydroformylation reactions may involve a liquid catalyst recycle procedure. Such liquid catalyst recycle procedures are known as seen disclosed, e.g., in U.S. Pat. Nos. 4,668,651; 4,774,361; 5,102,505 and 5,110,990. For instance, in such liquid catalyst recycle procedures it is common place to continuously or intermittently remove a portion of the liquid reaction product medium, containing, e.g., the aldehyde product, the solubilized metal-organophosphorus complex catalyst, free ligand, and organic solvent, as well as by-products produced in situ by the hydroformylation, e.g., aldehyde condensation by-products etc., and unreacted olefinic starting material, carbon monoxide and hydrogen (syn gas) dissolved in said medium, from the hydroformylation reactor, to a distillation zone, e.g., a vaporizer/separator wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner as discussed above. The remaining non-volatilized liquid residue which contains metal-organophosphorus complex catalyst, solvent, free organophosphorus ligand and usually some undistilled aldehyde product is then recycled back, with or with out further treatment as desired, along with whatever by-product and non-volatilized gaseous reactants that might still also be dissolved in said recycled liquid residue, in any conventional manner desired, to the hydroformylation reactor, such as disclosed e.g., in the above-mentioned patents. Moreover, the reactant gases so removed by such distillation from the vaporizer may also be recycled back to the reactor if desired.

In an embodiment of this invention, the aldehyde mixtures may be separated from the other components of the crude reaction mixtures in which the aldehyde mixtures are produced by any suitable method. Suitable separation methods include, for example, solvent extraction, crystallization, distillation, vaporization, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A preferred method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, both incorporated herein by reference.

More particularly, distillation and separation of the desired aldehyde product from the metal-organophosphorus complex catalyst containing product solution may take place at any suitable temperature desired. In general, it is recommended that such distillation take place at relatively low temperatures, such as below 150° C., and more preferably at a temperature in the range of from about 50° C. to about 130° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures or below on up to total gas pressure of about 50 psig should be sufficient for most purposes.

The generic scope of this invention includes a process for preparing carboxylic acids by oxidizing an aldehyde with a peracid in the presence of an amine and/or amine N-oxide catalyst to produce the carboxylic acid. The generic scope of this invention is not intended to be limited in any manner by any particular aldehyde-forming reaction.

Oxidation

Other aldehydes which may be useful in the process of this invention include, for example, 2-phenylpropionaldehyde, 2-(p-isobutylphenyl) propionaldehyde, 2-(6-methoxy-2-naphthyl) propionaldehyde, 2-(3-benzoylphenyl)-propionaldehyde, 2-(p-thienoylphenyl)propionaldehyde, 2-(3-fluoro-4-phenyl)phenylpropionaldehyde, 2-[4-(1,3-dihydro-1-oxo-2H-isoindol-2-yl)phenyl]propionaldehyde, 2-(2-methylacetaldehyde)-5-benzoylthiophene and the like. Illustrative of suitable aldehyde (including derivatives of aldehydes) and olefin starting material compounds include those permissible aldehyde and olefin starting material compounds which are described in Kirk-Othmer, Encyclopedia of Chemical Technology, Third Edition, 1984, the pertinent portions of which are incorporated herein by reference.

Once the requisite aldehyde product has been provided, the next step of the process of this invention involves oxidizing the aldehyde with a peracid in the presence of an amine and/or amine N-oxide catalyst to produce a carboxylic acid. Suitable solutions can be provided by using liquid aldehydes or by melting solid aldehydes. However, suitable solutions usually consist of the aldehydes dissolved in an appropriate solvent (e.g., in the solvent in which the first step of the process of this invention was conducted). Any solvent which will dissolve the aldehyde product and is unreactive with peracids may be used. Examples of suitable solvents are ketones (e.g., acetone), esters (e.g., ethyl acetate), hydrocarbons (e.g., toluene), nitrohydrocarbons (e.g., nitrobenzene), ethers (e.g., tetrahydrofuran (THF) and 1,2-dimethoxyethane) and water. A mixture of two or more solvents can be employed to maximize the purity and yield of the desired aldehyde. The solution used may also contain materials present in the crude reaction product of the aldehyde-forming reaction (e.g., catalyst, ligand and heavies). Preferably, however, the solution consists essentially of only the aldehyde and the solvent. The concentration of the aldehyde in the solvent solution will be limited by the solubility of the aldehyde in the solvent.

The oxidizing agent useful in the process of this invention is a peracid. Illustrative peracids include, for example, peracetic acid, performic acid, perpropionic acid, perbenzoic acid and the like. The preferred oxidizing agent is anhydrous peracetic acid. Such peracid oxidizing agents are well known in the art and can be used in amounts described below and in accordance with conventional methods.

The oxidizing agent is employed in an amount sufficient to permit complete oxidation of the aldehyde. Preferably, the oxidizing agent stoichiometry can range from about 1 to about 10 molar equivalents with respect to aldehyde, preferably from about 1 to about 2 molar equivalents with respect to aldehyde, and most preferably from about 1 to about 1.3 molar equivalents with respect to aldehyde.

The catalysts useful in the oxidation step of the process of this invention include primary, secondary and tertiary amines and amine N-oxides and mixtures thereof. The catalysts have sufficient basicity to catalyze the oxidation of an aldehyde to a carboxylic acid. Illustrative primary, secondary and tertiary amine and amine N-oxide catalysts include, for example, aliphatic amines, aliphatic amine N-oxides, aromatic amines, aromatic amine N-oxides, heterocyclic amines, heterocyclic amine N-oxides, polymeric amines, polymeric amine N-oxides and the like, including mixtures thereof. Illustrative aliphatic amines include substituted and unsubstituted alkyl amines such as butylamine, diethylamine, triethylamine and the like including the N-oxides thereof. Illustrative aromatic amines (those in which nitrogen is attached directly to an aromatic ring) include substituted and unsubstituted anilines and the N-oxides thereof, e.g., aniline, toluidine, diphenylamine, N-ethyl-N-methylaniline, 2,4,6-tribromoaniline and the like. Illustrative heterocyclic amines (those in which nitrogen makes up a part of an aromatic or non-aromatic ring) include substituted and unsubstituted pyridines, pyrimidines, pyrrolidines, piperidines, pyrroles, purines and the like including the N-oxides thereof. Preferred oxidation catalysts include, for example, 2,6-lutidine N-oxide, 5-ethyl-2-methylpyridine, 5-ethyl-2-methylpyridine N-oxide, 4-methoxypyridine N-oxide and 2,5-lutidine N-oxide. Amine N-oxide catalysts are preferred oxidation catalysts and can affect, e.g., decrease, the amount of formate byproduct formed in the oxidation process of this invention. The amine and/or amine N-oxide catalyst preferably has a high boiling point so as to reduce or eliminate amine impurities resulting from the catalyst in the product.

As indicated above, the catalysts have sufficient basicity to catalyze the oxidation of an aldehyde to a carboxylic acid. Such basicity can result from the catalyst functioning as a Lewis base or a Bronsted-Lowry base. The catalysts should be basic enough to promote decomposition of any aldehyde-peracid adduct but relatively unreactive with regard to oxidation by peracid. The basicity of the catalysts should also be sufficient to favor the oxidation reaction to carboxylic acids over any competing aldehyde reactions.

The amine and/or amine N-oxide catalyst is employed in a catalytically effective amount, i.e., an amount sufficient to catalyze the oxidation reaction. Preferably, the amine and/or amine N-oxide stoichiometry can range from about 0.1 to about 10 molar equivalents with respect to aldehyde, preferably from about 0.5 to about 2 molar equivalents with respect to aldehyde, and most preferably from about 0.7 to about 1.2 molar equivalents with respect to aldehyde. The amine and/or amine N-oxide stoichiometry can affect the amount of formate byproduct formed in the process of this invention.

The catalysts used in the oxidation step of the process of this invention may optionally be supported. Advantages of a supported catalyst may include ease of catalyst separation. Illustrative examples of supports include alumina, silica gel, ion-exchange resins, polymeric supports and the like.

The process conditions employable in the oxidation step of the process of this invention are chosen to reduce formate byproducts.

The mode of addition of reaction ingredients in the oxidation step of the process of this invention is not narrowly critical. The mode of addition should be such that an carboxylic acid is obtained.

The oxidation step of the process of this invention may be conducted at a reaction temperature from about −25° C. or lower to about 60° C. Lower reaction temperatures may generally tend to minimize formate byproduct formation. When using amine N-oxides as catalysts, temperatures should not exceed about 25° C. to minimize methyl ketone formation when oxidizing alpha-methyl substituted benzylic aldehydes. In general, oxidations at reaction temperatures of about −10° C. to about 25° C. are preferred.

The oxidation step of the process of this invention is conducted for a period of time sufficient to produce a carboxylic acid. The exact reaction time employed is dependent, in part, upon factors such as temperature, nature and proportion of starting materials, and the like. The reaction time will normally be within the range of from about one-half to about 200 hours or more, and preferably from less than about one to about 10 hours.

The oxidation step in the process of this invention can be carried out in the liquid state and can involve a batch or continuous liquid recycle system. A batch system is preferred for conducting such processes. Preferably, such oxidation involves a batch homogeneous catalysis process wherein the oxidation is carried out in the presence of any suitable conventional solvent as further described herein.

The oxidation step of the process of this invention may be conducted in the presence of an organic solvent. Depending on the particular catalyst and reactants employed, suitable organic solvents include, for example, alcohols, alkanes, ethers, aldehydes, esters, acids, amides, amines, aromatics and the like. Any suitable solvent which does not unduly adversely interfere with the intended oxidation process can be employed and such solvents may include those heretofore commonly employed in known processes. Mixtures of one or more different solvents may be employed if desired. Solvents which partially or totally dissolve the aldehyde and do not react with peracids may be useful. Organic esters are preferred solvents. Water and water/ethanol mixtures may also be useful solvents. The amount of solvent employed is not critical to this invention and need only be that amount sufficient to provide the reaction medium with the particular substrate and product concentration desired for a given process. In general, the amount of solvent when employed may range from about 5 percent by weight up to about 95 percent by weight or more based on the total weight of the reaction medium.

As indicated above, the carboxylic acid-forming process of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the amine and/or amine N-oxide catalyst. The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The carboxylic acid-forming process of this invention is useful for preparing mixtures of substituted and unsubstituted carboxylic acids. Illustrative preferred carboxylic acids prepared by the oxidation process of this invention include, for example, 2-phenylpropionic acid, 2-(p-isobutylphenyl) propionic acid, 2-(6-methoxy-2-naphthyl)propionic acid, 2-(3-benzoylphenyl)propionic acid, 2-(p-thienoylphenyl) propionic acid, 2-(3-fluoro-4-phenyl)phenylpropionic acid, 2-[4-(1,3-dihydro-1-oxo-2H-isoindol-2-yl)phenyl]propionic acid and the like. Illustrative of suitable carboxylic acids which can be prepared by the processes of this invention include those permissible carboxylic acids which are described in Kirk-Othmer, Encyclopedia of Chemical Technology, Third Edition, 1984, the pertinent portions of which are incorporated herein by reference.

The carboxylic acids described herein is useful in a variety of applications, such as intermediates in the manufacture of chemical compounds, pharmaceutical manufacture and the like.

For purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover.

As used herein, the following symbols have the indicated meanings:

| | |
|---|---|
| mL | milliliter |
| g | grams |
| °C. | degrees centigrade |
| mmol | millimoles |
| min | minute |

The following example is provided to illustrate the process of this invention.

EXAMPLE 1

Oxidation Of Cyclohexanecarboxaldehyde To Cyclohexanecarboxylic Acid Using Lutidine N-Oxide As Catalyst To a stirred solution of 5.0 g (44.6 mmol) of cyclohexanecarboxaldehyde in n-butyl acetate (45 mL) cooled in a wet-ice bath (ca. 2° C.) was added 5.5 g (44.6 mmol) of 2,6-dimethylpyridine N-oxide (2,6-lutidine N-oxide). To this solution was then added slowly dropwise 24.6 mL (66.9 mmol) of a 23.0 weight percent solution of peracetic acid in ethyl acetate, at a rate slow enough such that the reaction temperature did not exceed 10° C. (ca. 20 min). After the initial exotherm, the temperature returned to 2° C., and the reaction was maintained at this temperature for an additional 4 hours. The cold reaction solution was then transferred into a separatory funnel, was diluted with n-butyl acetate (50 mL), and was washed with a 1% aqueous solution of sodium thiosulfate ($Na_2S_2O_3$, 50 mL). The butyl acetate layer was further washed with two portions of water (50 mL each), and the combined water washes were back-extracted with n-butyl acetate (50 mL). The combined butyl acetate layers were extracted with two portions of a 5% aqueous solution of sodium hydroxide (NaOH, 50 mL each). The combined NaOH solutions were acidified to pH=1 with a 10% aqueous solution of hydrochloric acid. The resulting solution was extracted with two portions of dichloromethane (75 mL each), and the extract was dried over anhydrous $Na_2SO_4$. The extract was filtered and concentrated in vacuo to give 6.0 g (99%) of cyclohexanecarboxylic acid, containing small levels of unidentified impurities.

Although the invention has been illustrated by the preceding example, it is not to be construed as being limited thereby; but rather, the invention encompasses the generic area as hereinbefore disclosed. Various modifications and embodiments can be made without departing from the spirit and scope thereof.

We claim:

1. A process for producing a carboxylic acid which process comprises oxidizing an aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the carboxylic acid, wherein said amine and/or amine N-oxide catalyst has a basicity sufficient to catalyze said oxidizing of the aldehyde to the carboxylic acid, and provided that when the peracid is performic acid, the aldehyde is other than an aromatic or heteroaromatic aldehyde.

2. The process of claim 1 in which the aldehyde is selected from 2-phenylpropionaldehyde, 2-(p-isobutylphenyl)propionaldehyde, 2-(6-methoxy-2-naphthyl)propionaldehyde, 2-(3-benzoylphenyl)-propionaldehyde, 2-(p-thienoylphenyl)propionaldehyde, 2-(3-fluoro-4-phenyl)phenylpropionaldehyde, 2-propionaldehyde and 2-(2-methylacetaldehyde)-5-benzoylthiophene.

3. The process of claim 1 in which the peracid is selected from peracetic acid, performic acid, perpropionic acid and perbenzoic acid.

4. The process of claim 1 in which the amine and/or amine N-oxide catalyst is selected from 2,6-lutidine N-oxide, 5-ethyl-2-methylpyridine, 5-ethyl-2-methylpyridine N-oxide, 4-methoxypyridine N-oxide and 2,5-lutidine N-oxide.

5. The process of claim 1 in which the carboxylic acid is selected from 2-phenylpropionic acid, 2-(p-isobutylphenyl)propionic acid, 2-(6-methoxy-2-naphthyl)propionic acid, 2-(3-benzoylphenyl)propionic acid, 2-(p-thienoylphenyl)propionic acid, 2-(3-fluoro-4-phenyl)phenylpropionic acid and 2-propionic acid.

* * * * *